(12) United States Patent
Lopez et al.

(10) Patent No.: US 11,583,206 B2
(45) Date of Patent: Feb. 21, 2023

(54) SENSING PLANTAR ADIPOSE TISSUE

(71) Applicant: HEWLETT-PACKARD DEVELOPMENT COMPANY, L.P., Spring, TX (US)

(72) Inventors: Matthew G. Lopez, San Diego, CA (US); Ryan Forcier, San Diego, CA (US); Brian R. Jung, San Diego, CA (US); Marvin Dav Hoag, San Diego, CA (US); Francis L. Kozakiewicz, San Diego, CA (US)

(73) Assignee: HEWLETT-PACKARD DEVELOPMENT COMPANY, L.P., Spring, TX (US)

( * ) Notice: Subject to any disclaimer, the term of this patent is extended or adjusted under 35 U.S.C. 154(b) by 180 days.

(21) Appl. No.: 16/756,805

(22) PCT Filed: Nov. 29, 2017

(86) PCT No.: PCT/US2017/063773
§ 371 (c)(1),
(2) Date: Apr. 16, 2020

(87) PCT Pub. No.: WO2019/108179
PCT Pub. Date: Jun. 6, 2019

(65) Prior Publication Data
US 2020/0237259 A1    Jul. 30, 2020

(51) Int. Cl.
*A61B 5/103* (2006.01)
*G01B 5/207* (2006.01)

(52) U.S. Cl.
CPC ............ *A61B 5/1036* (2013.01); *G01B 5/207* (2013.01); *A61B 2562/0247* (2013.01); *A61B 2562/0252* (2013.01)

(58) Field of Classification Search
CPC ... A61B 5/4827; A61B 5/0053; A61B 5/6829; A61B 5/1036; A61B 2560/04; A61B 2562/0247; A61B 2562/0252; G01B 5/207
See application file for complete search history.

(56) References Cited

U.S. PATENT DOCUMENTS 5,941,835 A * 8/1999 Sundman ............. A61B 5/1036
                                                      600/592
6,190,334 B1 * 2/2001 Lasky .................. A61B 5/0053
                                                      600/587
(Continued)

FOREIGN PATENT DOCUMENTS

CN    107174251        9/2017
JP    H11239573 A      9/1999
(Continued)

OTHER PUBLICATIONS

Storr, "Pulse Width Modulation" accessed with waybackmachine Apr. 27, 2022 archived Feb. 2011 (Year: 2011).*
(Continued)

*Primary Examiner* — Rene T Towa
*Assistant Examiner* — Alexander H Connor
(74) *Attorney, Agent, or Firm* — Shook, Hardy & Bacon L.L.P.

(57) ABSTRACT

In some examples, an apparatus comprises a platform having an upper surface to contact a plantar surface of a human foot positioned on the platform, a first pressure sensor to sense a pressure applied to the upper surface by a heel of the human foot, and a first probe extending through an opening in the platform and movable vertically upward through the opening to probe an adipose layer on a bottom of the heel. The apparatus also comprises a first actuator to displace the first probe upwardly against the adipose layer with a pre- (Continued)

determined force, and a linear displacement sensor to sense a vertical displacement of the first probe.

15 Claims, 4 Drawing Sheets

(56) References Cited

U.S. PATENT DOCUMENTS

| | | | |
|---|---|---|---|
| 7,736,315 | B2 | 6/2010 | Vanderby et al. |
| 9,021,677 | B1 | 5/2015 | Burns et al. |
| 2006/0178596 | A1* | 8/2006 | Robichaud ............ A61B 5/0053 600/587 |
| 2009/0099457 | A1 | 4/2009 | Barnes |
| 2010/0113966 | A1* | 5/2010 | Spruce .................... A61B 5/00 600/557 |
| 2012/0220892 | A1* | 8/2012 | Gandhi ................ A61B 5/0051 600/552 |
| 2019/0021649 | A1* | 1/2019 | Van Snellenberg . A61B 5/4041 |

FOREIGN PATENT DOCUMENTS

| | | |
|---|---|---|
| JP | 2001252258 A | 9/2001 |
| KR | 101445488-31 | 9/2014 |
| WO | WO-2005044105 A1 | 5/2005 |

OTHER PUBLICATIONS

Siddiqui, S. R. Alty, M. Spruce and S. E. Dudley, "Automated peripheral neuropathy assessment of diabetic patients using optical imaging and binary processing techniques," 2013 IEEE Point-of-Care Healthcare Technologies (PHT), 2013, pp. 200-203, doi: 10.1109/PHT.2013.6461319. (Year: 2013) (Year: 2013).*

Parker et al., "A Device for Characterising the Mechanical Properties of the Plantar Soft Tissue of the Foot," Aug. 12, 2015, Medical Engineering and Physics 37 (2015), pp. 1098-1104.

HPDC. "International Search Report and Written Opinion," dated Aug. 29, 2018, PCT Pat. App. No. PCT/US2017/063773, 7 p.

* cited by examiner

SENSING PLANTAR ADIPOSE TISSUE

BACKGROUND

A normal human foot includes deposits of adipose tissue located beneath the heel bone and metatarsal heads. These viscoelastic fat pads disperse pressure and reduce shock during walking or running.

BRIEF DESCRIPTION OF THE DRAWINGS

Various examples are described below referring to the following figures.

DETAILED DESCRIPTION

Figure 1:
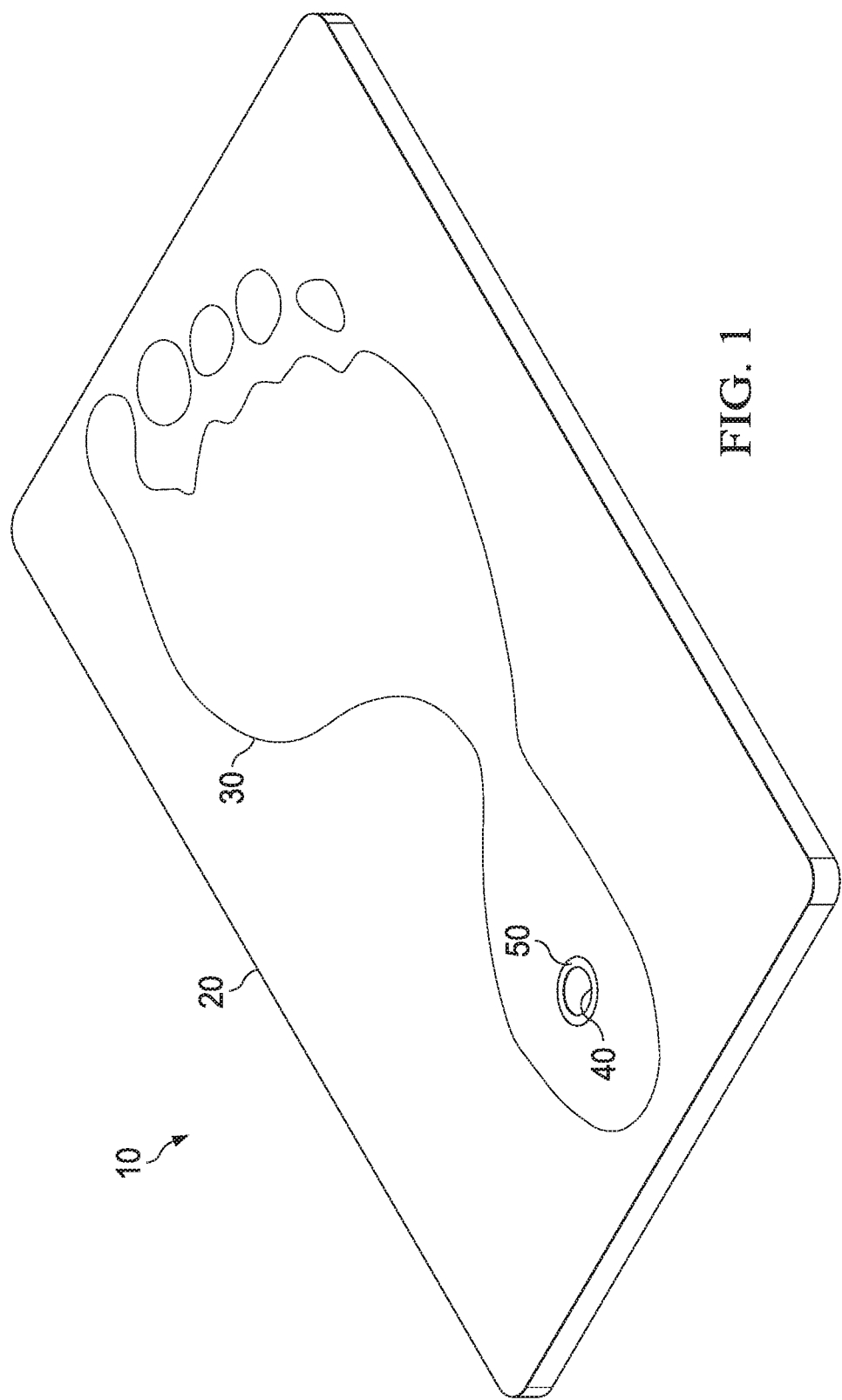
FIG. 1 is a perspective view showing a measuring device in accordance with various examples.

Various factors, including age, prolonged exercise, injury, and disease may deplete or reduce the effectiveness of plantar adipose tissue. In such cases, orthotic cushioned insoles may help supplement the function of the adipose tissue and help prevent pain or injury. However, as between different individuals, plantar adipose tissue may vary in position, shape, thickness, and contour. Thus, in order to increase their effectiveness, orthotic cushioned insoles should be customized to a particular individual.

Existing solutions may not adequately characterize plantar adipose tissue for the purpose of customizing orthotic cushioned insoles. For instance, existing solutions for use in a retail environment typically include a pressure plate to measure the pressure distribution under a human foot to help identify the location of the arch and to assess the foot volume. More complicated systems may be used in a doctor's office or other healthcare setting. For example, various devices may use x-ray, ultrasound, or computerized tomography (CT) scanning technology to characterize the structure of the plantar adipose tissue. Unfortunately, these methods are not well-suited for use in a retail environment where a consumer may wish to purchase customized orthotic cushioned insoles without incurring significant expense.

In accordance with the present disclosure, devices are provided to measure the viscoelasticity of the plantar adipose tissue on the bottom of a human foot. Such a characterization of the adipose layer is helpful for many purposes, including in the manufacture of customized orthotic cushioned insoles. Examples of devices in accordance with the present disclosure are less complicated and may be more suitable for use in a retail environment. First, a human places his or her foot on a platform at a predetermined location. The platform includes pressure sensors for measuring the pressure exerted on the platform by the plantar surface of the foot. For example, such pressure sensors may be included near the area of the heel of the foot in order to measure the pressure placed on the platform near the area of the heel.

The devices may also include a probe which extends vertically upwardly through an opening in the platform. The probe is used for probing the adipose layer on the foot at predetermined locations, for example, at the center of the heel at a location nearby a pressure sensor. In this process, the probe is moved upwardly through the opening by an actuator that is configured to apply a predetermined upward force to the probe upon contacting a localized area of the adipose layer. The adipose layer is thereby compressed and the vertical displacement of the probe into the adipose layer is measured by a linear displacement sensor. A characterization of the adipose layer is thus provided by the sensed vertical displacement of the probe into the adipose layer, the predetermined force applied to the probe, and by the pressure sensed on the top of the platform by the pressure sensor.

The devices may alternatively include pressure sensors for measuring the pressure placed on the platform at dispersed locations. For example, an array of pressure sensors may be provided so that the pressure may be sensed near several locations on the plantar surface at areas of interest for characterizing the adipose layer, for example, at areas near the heel and near the metatarsal heads.

Alternatively, a more detailed characterization of the adipose layer may be provided by applying a series of successively increasing forces to the probe, and by simultaneously measuring the displacement of the probe at each successive pressure. The series of forces and displacements may provide such a more detailed characterization of the adipose layer.

Referring now to FIG. 1, there is shown an example of a measuring device 10 which includes a platform 20 on which a person stands with his or her bare foot. The platform 20 may include visible markings on the top surface to help guide a person in placing his or her foot in a particular location on the platform 20. For example, platform 20 may have an outline 30 of a human foot that is painted or printed on the top surface. Alternatively, platform 20 may include lights or a projected image (not shown) to help guide the placement of a human foot.

Platform 20 may include a vertical hole 40 extending therethrough and positioned near the center of the expected location of the heel being measured. Nearby or adjacent to the hole 40 is a pressure sensor, such as a load cell 50 surrounding hole 40. Load cell 50 senses the pressure created by the heel of the person standing on platform 20 near the area surrounding the hole 40. As explained below, vertical hole 40 is provided so that a probe may extend through the platform from below and compress a localized area on the bottom of the person's heel being measured.

Alternatively, a pressure plate (not shown) may be provided on the top surface of the platform 20 across a broad area where the human foot is placed. Such a pressure plate collects an array of pressures acting on the platform 20 across the area of the foot. Such a pressure plate may use any of a variety of technologies, including elastic-resistive membranes, to collect the foot pressure data.

Figure 2:
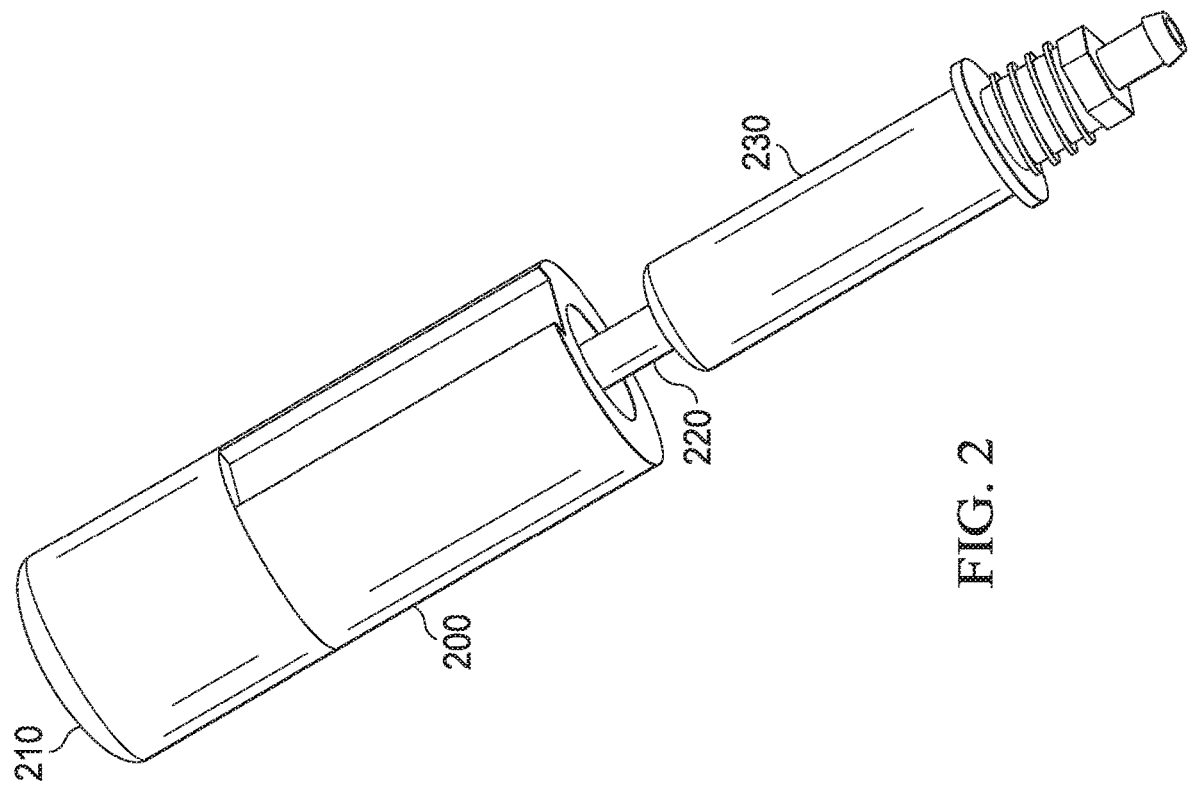
FIG. 2 is a perspective view showing a probe, actuator, and displacement sensor in accordance with various examples.

FIG. 2 illustrates an example probe 200 having a stainless steel probe tip 210 positioned on its upper end. In use, the probe tip 210 extends upwardly through the hole 40 (FIG. 1) and compresses the plantar adipose tissue with a predetermined force. Probe tip 210 may be circular having a 1 centimeter diameter and may be slightly rounded to prevent discomfort when pressing against human tissue. The probe tip 210 is positioned on top of a linear displacement sensor, such as a linear variable differential transformer (LVDT) 220 as shown in FIG. 2. LVDT 220 senses the vertical displacement of the probe tip 210 into the plantar adipose tissue when a predetermined force is applied to the probe tip 210.

The probe 200 also includes a linear actuator to displace the probe tip 210 vertically upward and into the plantar adipose tissue with a predetermined force. For example, the actuator illustrated in FIG. 2 is a pneumatic cylinder 230 which is attached to LVDT 220 so that the application of a predetermined pneumatic pressure creates a predetermined upward force, while LVDT 220 senses displacement of the probe tip 210.

Figure 3:
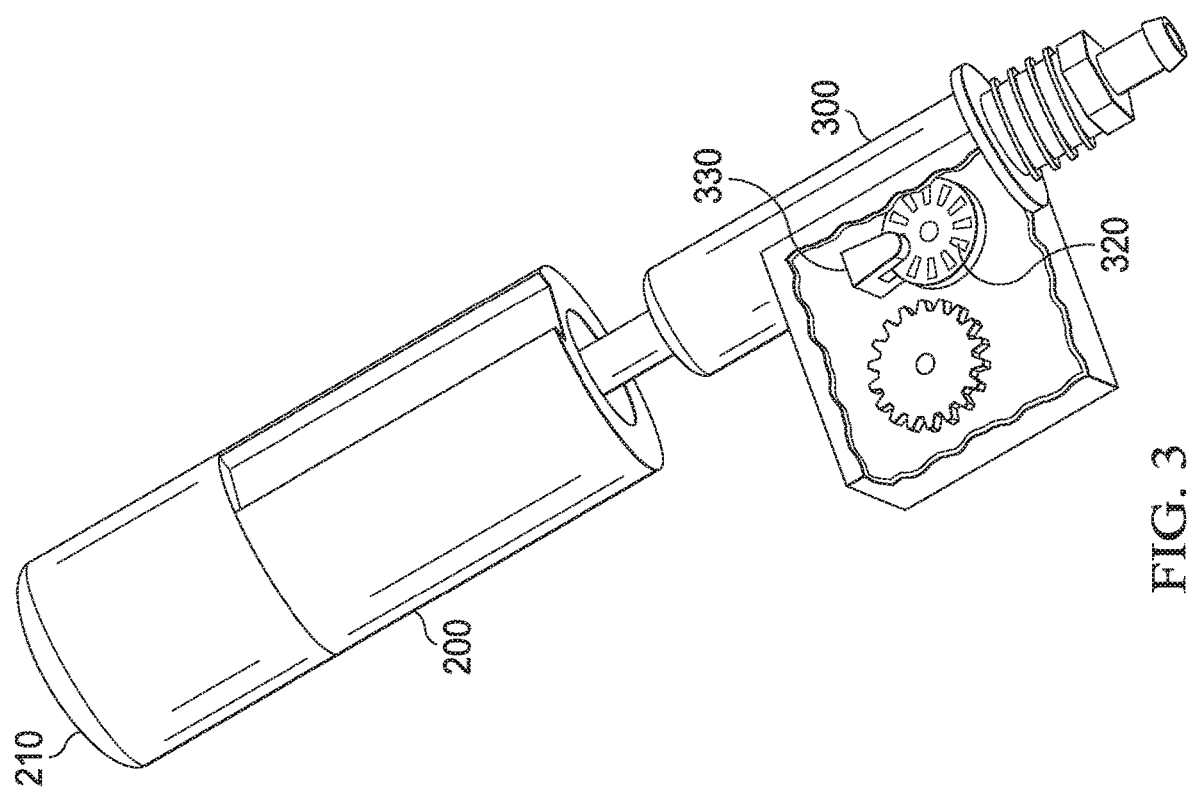
FIG. 3 is a partial cutaway perspective view showing a probe, an actuator, and a displacement sensor in accordance with various examples.

Referring now to FIG. 3, in some examples, the actuator may also be a servo linear actuator 300. Servo linear actuator 300 may operate using an internal stepper motor (not shown) to displace the probe tip 210. By way of example, servo linear actuator 300 may be activated by a pulse width modulation (PWM) signal so that a predetermined stalling force may be applied by the servo linear actuator 300 according to the duty cycle of the PWM signal, e.g., a 50% duty cycle may supply 50% of the force that would be applied at a 100% duty cycle. In addition, one of the rotating gears or other rotating parts which operate the servo linear actuator 300 may include encodings 320 at periodic circumferential positions. The servo linear actuator 300 may also include a decoder 330 positioned nearby the location of the encodings 320 in order to sense each time that one of the encodings 320 passes by the decoder 330. Sensing these encodings 320 provides a way to sense the displacement of the actuator 300. In this manner, the servo linear actuator 300 may also operate as a linear displacement sensor without the need for additional hardware.

Figure 4:
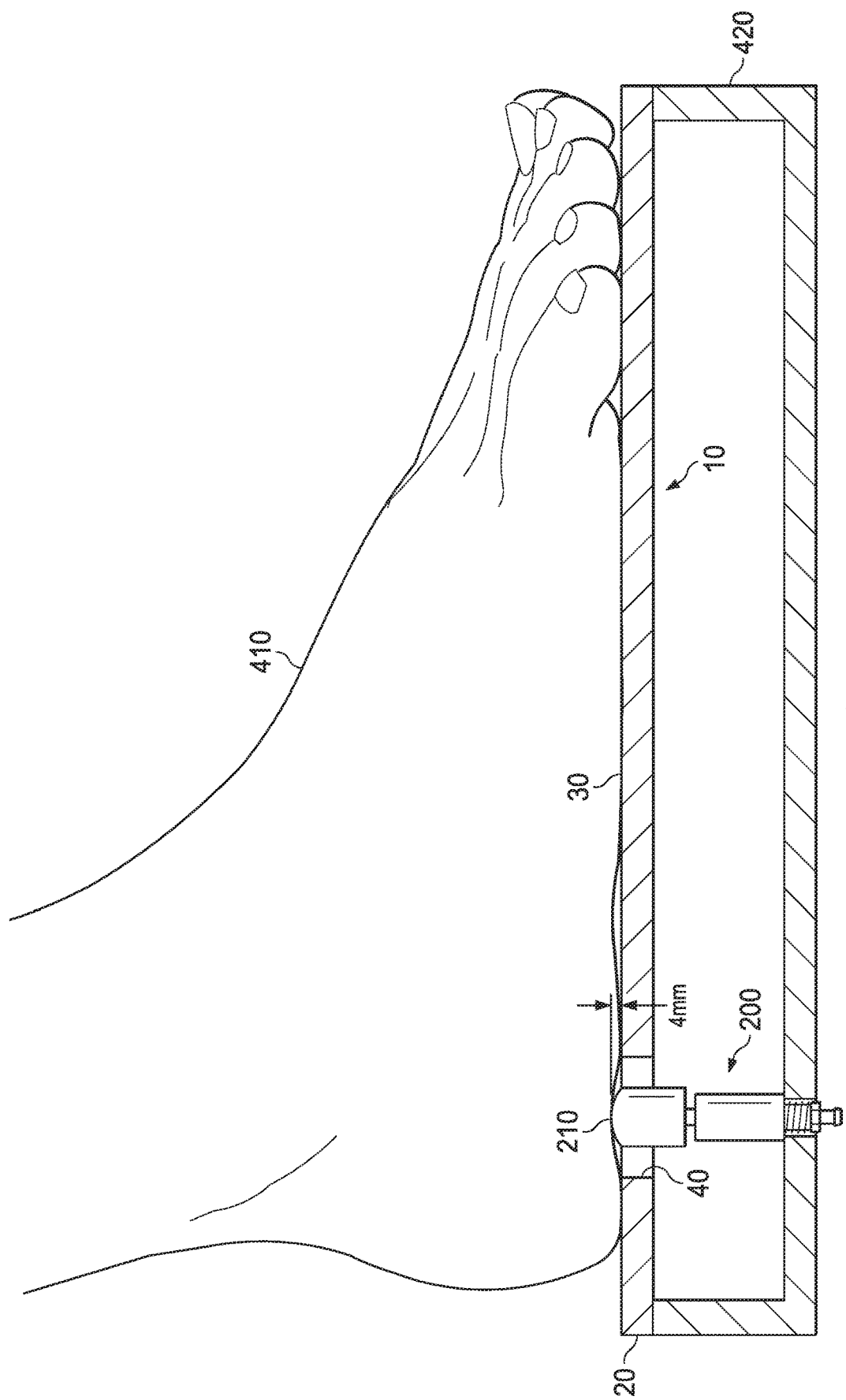
FIG. 4 is a partial cross section side view of a foot placed on a measuring device in accordance with various examples.

As shown in FIG. 4, during operation, a human stands on the platform 20 by placing his or her foot 410 in the position designated by outline 30 (FIG. 1) so that the center of the person's heel is above the hole 40. The probe tip 210 is then displaced upwardly with a predetermined force by the actuator, such as pneumatic cylinder 230 or servo linear actuator 300 (FIGS. 2 and 3).

Upon the application of the predetermined force, the linear displacement sensor, such as the LVDT 220 or encodings 320 and decoder 330 (FIGS. 2 and 3), sense the linear displacement of the probe tip 210 into the adipose layer. For example, the displacement is shown as 4 millimeters in FIG. 4. Together with the pressure applied to the surface of the platform 20 adjacent to the hole 40, this measured linear displacement of the probe tip 210 into the adipose layer at a predetermined force provides a standard methodology to characterize of the compressibility of the adipose layer. This data may then be used to assist in the manufacturing or selection of custom cushioned orthotic insoles.

A more detailed characterization of the plantar adipose tissue may be obtained by applying a series of several increasing predetermined forces and measuring the displacement of probe tip 210 into the adipose layer at each of the forces in the series of predetermined forces. By way of example, the force may be applied in 10 increasing steps and the displacement of probe tip 210 measured at each of the 10 steps.

Figure 5:
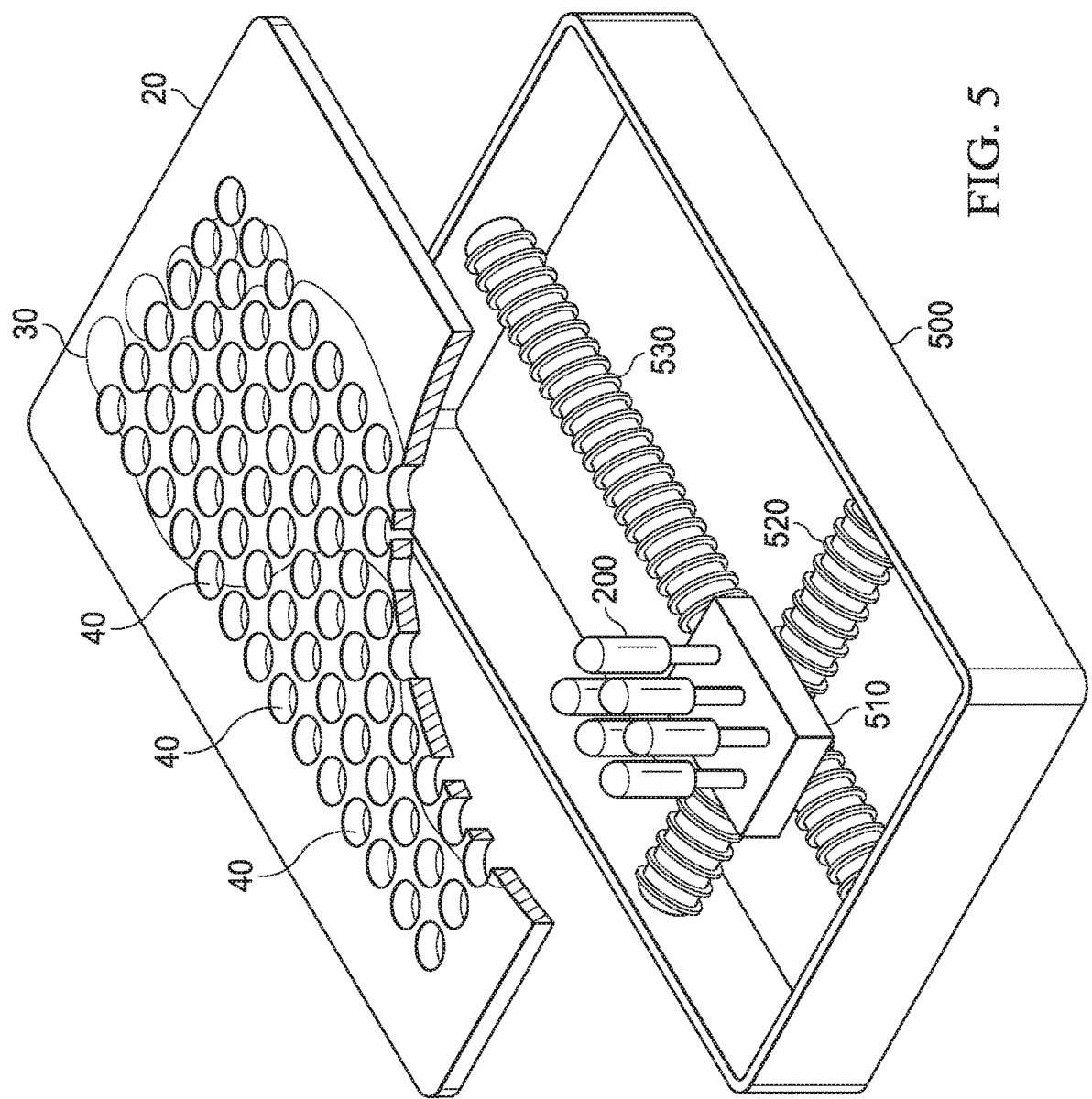
FIG. 5 is a partial cutaway perspective view showing a measuring device in accordance with various examples.

Alternatively, as shown in FIG. 5, a larger array of several probes 200 may be dispersed across the platform 20 throughout substantially the entire area of the foot, or spread across particular areas of interest, such as under the heel and under the metatarsal pads near the forefoot (not shown). Such an array of probes 200 may include any of the actuator and linear displacement sensor components as described above in connection with FIGS. 2 and 3. Each of these probes 200 is displaced upwardly through a corresponding hole 40 and adjacent load cell 50 in the platform 20. When multiple probes 200 are dispersed across substantially the entire area of the foot, a separate pressure plate or other discrete pressure sensor on the top of the platform 20 may no longer be required. In these circumstances, certain of the probes 200 may measure the compressibility of the adipose tissue, while the remaining probes 200 may be used to sense the surrounding pressure applied across the area of platform 20.

When multiple probes 200 are employed, such as illustrated in FIG. 5, the predetermined force applied to each probe 200 may be equal for each probe 200. Alternatively, the force applied to a probe 200 at one location may differ from the force applied to a probe 200 located at a different location, in part to account for expected differences in the adipose layer at different locations on the bottom of a foot. For example, the predetermined force applied to a probe 200 near the heel may differ from the predetermined force applied to a probe 200 near the forefoot.

The probes 200 and platform 20 may be supported by one of several different mechanisms. When a single or multiple probes 200 are employed, the actuator for each probe may be mounted on a base 420, as illustrated for a single actuator in FIG. 4. In addition, a single probe 200 or a group of multiple probes 200 may be mounted on an X-Y stage table 500, such as illustrated in FIG. 5.

The X-Y stage table 500 may include a stage platform 510 for mounting the single probe 200 or a group of probes 200. For example, FIG. 5 illustrates 6 probes 200 mounted on stage platform 510. The X-Y stage table 500 includes a translation member 520 which translates the stage platform 510 in the X-direction left and right across the foot, and a translation member 530 which translates the stage platform 510 in the Y-direction forward and backward along the length of the foot. The stage platform 500 may be configured to move parallel to the plane formed by the platform 20 by aligning the X-translation member 520 and the Y-translation member with the plane formed by the platform 20. In this manner, the stage platform 510 with probe 200 or multiple probes 200 mounted thereon may be moved to any desired location under the foot. Movement of the stage platform 510 thereby facilitates the measurement of the adipose layer at multiple locations using fewer probes 200, and may also be used to account for errors in positioning the foot at a particular location on platform 20.

Any of the foregoing exemplary devices may provide a sufficiently simple and cost-effective means for directly measuring the plantar adipose tissue for the purpose of manufacturing or selecting custom orthotic cushioned insoles, even in a retail setting, and without the necessity of medical professionals or complex diagnostic equipment.

The above discussion is meant to be illustrative of the principles and various examples of the present disclosure. Numerous variations and modifications will become apparent to those skilled in the art once the above disclosure is fully appreciated. It is intended that the following claims be interpreted to embrace all such variations and modifications.

What is claimed is:

1. An apparatus comprising:
    a platform having an upper surface adapted to contact a plantar surface of a human foot positioned on the platform;
    a first pressure sensor adapted to sense a pressure applied to the upper surface by a heel of the human foot;
    a first probe extending through an opening in the platform and moveable vertically upward through the opening adapted to probe an adipose layer on a bottom of the heel;

a second probe adapted to probe the adipose layer on the bottom of the heel;

a first actuator adapted to displace the first probe upwardly against the adipose layer with a predetermined force;

a second actuator adapted to displace the second probe, wherein the second actuator and the second probe are mounted on a X-Y stage positioned below the platform and selectively translatable in an X-direction and a Y-direction; and a first linear displacement sensor adapted to sense a vertical displacement of the first probe against the adipose layer.

2. The apparatus of claim 1 wherein the first actuator comprises pneumatic cylinder.

3. The apparatus of claim 1 wherein the first linear displacement sensor comprises a linear variable differential transformer.

4. The apparatus of claim 1 wherein the first actuator is a servo linear actuator which is activated by a pulse width modulation signal.

5. The apparatus of claim 4 wherein the first linear displacement sensor includes a decoder adapted to sense encodings located at predetermined locations on the first actuator.

6. The apparatus of claim 1 wherein
the first actuator displaces upwardly with a series of increasing predetermined forces; and
the first linear displacement sensor senses a series of vertical displacements of the first probe corresponding to the series of increasing predetermined forces.

7. The apparatus of claim 1 further comprising:
a second pressure sensor adapted to sense a second pressure applied to the upper surface by a metatarsal area of the human foot;
the second probe extending through a second opening in the platform and moveable vertically upward through the second opening adapted to probe the adipose layer on a bottom of the metatarsal area;
the second actuator adapted to displace the second probe upwardly against the adipose layer with another predetermined force; and
a second linear displacement sensor adapted to sense a second vertical displacement of the second probe against the adipose layer.

8. The apparatus of claim 7 wherein the first actuator and second actuator are activatable by a pulse width modulation signal having a duty cycle that corresponds with a predetermined stalling force to be applied by the first actuator and second actuator.

9. The apparatus of claim 1 further comprising:
a plurality of second probes extending through a plurality of second openings dispersed over an area of the platform and moveable vertically upward through the second openings adapted to probe a plurality of locations of plantar adipose tissue;
a plurality of second actuators connected to the plurality of second probes adapted to displace the probes upwardly against the plantar adipose tissue with another predetermined force; and
a plurality of second linear displacement sensors adapted to sense a vertical displacement of the plurality of second probes,
wherein the plurality of second probes and plurality of second actuators comprise a plurality of second pressure sensors adapted to sense a plurality of second pressures applied to the upper surface by the human foot.

10. An apparatus comprising:
a platform having an upper surface adapted to contact a plantar surface of a human foot positioned on the platform, wherein the platform includes first and second openings;
a first probe adapted to probe an adipose layer on a bottom of the foot above the first opening;
a second probe adapted to probe the adipose layer on the bottom of the foot above the second opening, wherein the first probe and the second probe are selectively positionable below the platform under the first and second openings such that the first probe and second probe may be selectively adapted to probe the adipose layer on the bottom of the foot above the first and second openings;
a first servo linear actuator adapted to displace the first probe upwardly against the adipose layer with a predetermined force, and to sense a vertical displacement of the first probe; and
a second servo linear actuator adapted to displace the second probe upwardly against the adipose layer with another predetermined force, and to sense a vertical displacement of the second probe.

11. The apparatus of claim 10 wherein the platform forms third and fourth openings, and the first probe and the second probe are selectively positionable below the platform under the third and fourth openings, such that the first probe and second probe may selectively probe the adipose layer on the bottom of the foot above the third and fourth openings.

12. The apparatus of claim 10 wherein:
the first servo linear actuator and the second servo linear actuator have a stalling force that corresponds with a duty cycle of a pulse width modulation signal received by the first actuator and the second actuator; and
the first servo linear actuator and the second servo linear actuator include rotary encodings and a decoder adapted to sense the encodings, such that the first servo linear actuator and the second servo linear actuator sense a respective vertical displacement of the first probe and the second probe.

13. An apparatus comprising:
a platform having an upper surface adapted to contact a plantar surface of a human foot positioned on the platform, wherein the platform forms first and second openings which extend vertically through the platform;
a first probe adapted to probe an adipose layer on a bottom of the foot;
a second probe adapted to probe the adipose layer on the bottom of the foot;
a first actuator adapted to displace the first probe upwardly against the adipose layer;
a second actuator adapted to displace the second probe;
a linear displacement sensor adapted to sense a vertical displacement of the probe against the adipose layer; and
an X-Y stage positioned below the platform and selectively translatable in an X-direction and a Y-direction, wherein the first actuator and probe are mounted on the X-Y stage to selectively translate the first actuator and probe from beneath the first opening to beneath the second opening, and
wherein the second actuator and second probe are mounted on the X-Y stage.

14. The apparatus of claim 13 wherein the platform is parallel to a plane formed by the X-direction and the Y-direction of the X-Y stage.

15. The apparatus of claim 13 including:
and
a second linear displacement sensor adapted to sense a vertical displacement of the second probe.

\* \* \* \* \*